US00PP24109P2

(12) United States Plant Patent
Bergman

(10) Patent No.: US PP24,109 P2
(45) Date of Patent: Dec. 24, 2013

(54) *CHRYSANTHEMUM* PLANT NAMED 'CIDZ0035'

(50) Latin Name: *Chrysanthemum×morifolium*
Varietal Denomination: CIDZ0035

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 65 days.

(21) Appl. No.: 13/506,880

(22) Filed: May 22, 2012

(51) Int. Cl.
*A01H 5/00* (2006.01)

(52) U.S. Cl.
USPC ..... Plt./295

(58) Field of Classification Search
USPC ..... Plt./295
See application file for complete search history.

*Primary Examiner* — Annette Para
(74) *Attorney, Agent, or Firm* — Joshua L. Price

(57) ABSTRACT

A new *Chrysanthemum* plant named 'CIDZ0035' particularly distinguished by the yellow-orange colored, daisy-spoon type inflorescences, vigorous growth habit and an 8 week flowering response time.

1 Drawing Sheet

Latin name of the genus and species of the plant claimed: *Chrysanthemum×morifolium.*

Varietal denomination: 'CIDZ0035'.

BACKGROUND OF THE NEW PLANT

The present invention comprises a new *Chrysanthemum*, botanically known as *Chrysanthemum×morifolium*, and hereinafter referred to by the variety name 'CIDZ0035'.

'CIDZ0035' is a product of a planned breeding program. The new cultivar has yellow-orange colored, daisy-spoon type inflorescences, vigorous growth habit and an 8 week flowering response time.

'CIDZ0035' originates as a natural whole plant mutation of 'Syngold Emporia', U.S. Plant Pat. No. 22,436. 'CIDZ0035' was discovered and selected by the inventor as a single flowering plant within a population of the parent cultivar, growing in pots under a shade structure in Fort Myers, Fla., in March 2009. The parent cultivar 'Syngold Emporia' has golden colored inflorescences, slightly longer foliage length, somewhat darker petioles and shorter peduncles compared to 'CIDZ0035'.

The first act of asexual reproduction of 'CIDZ0035' was accomplished when vegetative cuttings were propagated from the initial selection in June 2009 in a greenhouse in Fort Myers, Fla.

BRIEF SUMMARY OF INVENTION

Horticultural examination of plants grown from cuttings of the plant initiated in June 2009, and continuing thereafter, has demonstrated that the combination of characteristics as herein disclosed for 'CIDZ0035' are firmly fixed and are retained through successive generations of asexual reproduction.

'CIDZ0035' has not been observed under all possible environmental conditions. The phenotype may vary significantly with variations in environment such as temperature, light intensity, and day length.

Plant Breeder's Rights for this cultivar were applied for in Canada on Jul. 29, 2011, No. 11-7351 and in Brazil on Aug. 14, 2012, No. 218060001842012. 'CIDZ0035' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0035' with colors being as true as possible with an illustration of this type.

The photographic drawing shows 4 flowering plants of the new variety, and a close-up of the flowers.

DETAILED BOTANICAL DESCRIPTION

The plant descriptions, measurements and aforementioned photographs were taken in Gilroy, Calif. in January 2012 under natural light. These plants were grown 4 plants in a 5 inch pot under center bud removal and blackcloth controlled greenhouse trial conditions in Gilroy, Calif. These plants were 10-12 weeks old.

Color references are made to The Royal Horticultural Society Colour Chart (R.H.S.) 2001.

TABLE 1

DIFFERENCES BETWEEN THE NEW VARIETY 'CIDZ0035' AND A MOST SIMILAR VARIETY

| | 'CIDZ0035' | 'Syngold Emporia' (U.S. Plant Pat. No. 22,436) |
|---|---|---|
| Foliage length: | Slightly shorter | Slightly longer |
| Petiole color: | Somewhat lighter | Somewhat darker |
| Peduncle length: | Somewhat longer | Somewhat shorter |

Plant:

*Form, growth and habit.*—Herbaceous, pot-type, stems upright, freely branching, moderately vigorous growth habit.

*Plant height.*—21.0-22.0 cm.

*Plant height (inflorescence included).*—28.0-30.0 cm.

*Plant width.*—24.5-30.0 cm.

Roots:
*Number of days to initiate roots.*—4 days at about 22 degrees C.
*Number of days to produce a rooted cutting.*—About 10 days at 22 degrees C.
*Type.*—Fine, fibrous, free branching.
*Color.*—RHS N155B but whiter.

Foliage:
*Arrangement.*—Alternate.
*Immature, leaf color, upper surface.*—Closest to RHS 147A. Lower surface: Closest to RHS 147B.
*Mature, leaf color, upper surface.*—Closest to RHS 147A with some RHS 147B mottling. Lower surface: Closest to RHS 147B.
*Length.*—8.0-8.5 cm.
*Width.*—5.5-5.8 cm.
*Shape.*—Ovate.
*Base shape.*—Attenuate.
*Apex shape.*—Mucronulate.
*Margin.*—Palmately lobed; irregularly incised, slightly serrate.
*Texture, upper surface.*—Bifid T-shaped hairs.
*Lower surface.*—Bifid T-shaped hairs.
*Color of veins, upper surface.*—Closest to RHS 144B becoming indistinct.
*Color of veins, lower surface.*—Closest to RHS 144B.
*Pattern of veining.*—Palmate.
*Petiole color.*—RHS 144B.
*Length.*—2.0-2.5 cm.
*Diameter.*—0.3-0.4 cm.
*Texture.*—Bifid T-shaped hairs.

Stem:
*Quantity of main branches per plant.*—3-4.
*Color of stem.*—RHS 137C but appears lighter due to hair.
*Length of stem.*—15.0-20.0 cm.
*Diameter.*—0.4-0.5 cm.
*Length of internodes.*—0.5-2.0 cm.
*Texture.*—Bifid T-shaped hairs.
*Color of peduncle.*—RHS 137C but appears lighter due to hair.
*Length of peduncle.*—4.0-7.0 cm.
*Peduncle diameter.*—0.25-0.35 cm.
*Texture.*—Bifid T-shaped hairs.

Inflorescence:
*Type.*—Compositae type, solitary daisy spoon-type inflorescences, borne terminally above foliage, ray florets arranged acropetally on a capitulum.
*Quantity of short days to flowering (response time).*—About 8 weeks.
*Natural season flowering.*—Not determined on this variety.
*Quantity of inflorescences per plant.*—15-22 with 3-6 buds.
*Lastingness of individual blooms on the plant.*—About 4 weeks.
*Fragrance.*—Slightly spicy.

Bud (just when opening/showing color):
*Color.*—RHS 1C quickly becoming more overlaid with very light hue of RHS 26C.
*Length.*—1.3-2.0 cm.
*Width.*—1.3-1.5 cm.
*Shape.*—Oblate.

Immature inflorescence:
*Diameter.*—5.4-8.0 cm.
*Color of ray florets, upper surface.*—RHS 14B ground color overlaid with a little deeper hue than RHS 31B. Lower surface: RHS 14C.

Mature inflorescence:
*Diameter.*—10.0-11.0 cm.
*Depth.*—3.0-3.5 cm when inflorescence is completely flattened out.
*Total diameter of disc.*—1.8-2.0 cm.
*Receptacle color.*—RHS 144B.
*Receptacle height.*—0.4-0.5 cm.
*Receptacle diameter.*—0.7-0.8 cm.

Ray florets:
*Average quantity of florets.*—30-33 in 1-2 whorls.
*Color of florets, upper surface.*—RHS 15C overlaid with a little deeper hue than RHS 31B. Lower surface: RHS 12C.
*Length.*—5.0-5.7 cm.
*Width.*—At widest point varies 0.5-0.8 cm.
*Shape.*—Spoon.
*Apex shape.*—Mostly slightly cuspidate, with some obtuse or irregularly emarginate.
*Margin.*—Entire.
*Texture, upper surface.*—Papillose. Lower surface: Papillose.

Disc florets:
*Average quantity of florets.*—Approximately 250.
*Color of florets.*—RHS 145C basally with RHS 3B to RHS 3C at the apex.
*Length.*—0.5 cm.
*Width.*—0.1 cm.
*Shape.*—Tubular, elongated.
*Apex shape.*—Acute, 5 pointed.

Phyllaries:
*Quantity.*—24-29.
*Color, upper surface.*—RHS 146B. Lower surface: Closest to RHS 146A.
*Length.*—0.5-0.7 cm.
*Width.*—0.1-0.15 cm.
*Shape.*—Lanceolate.
*Apex shape.*—Acute.
*Base.*—Fused.
*Margins.*—Entire; papery.
*Texture, upper surface.*—Glabrous. Lower surface: Bifid T-shaped hairs.

Reproductive organs:
*Pistil.*—1, found on both types of florets.
*Length.*—0.7 cm.
*Style color.*—RHS 1C.
*Style length.*—0.6 cm.
*Stigma color.*—RHS 1B.
*Stigma shape.*—Bi-parted.
*Ovary color.*—RHS 155C but more translucent.
*Ovary length.*—0.05 cm.
*Ovary width.*—0.05 cm.
*Stamens.*—4, found on only on the disc florets.
*Color of filaments.*—RHS 155B.
*Length filaments.*—0.4 cm.
*Anther color.*—RHS 13A.
*Anther length.*—0.15 cm.
*Anther shape.*—Ovate.
*Color of pollen.*—RHS 17B.
*Pollen amount.*—Abundant.

Fertility/seed set: Has not been observed to date.
Disease/pest resistance: Has not been observed to date.

What is claimed is:

1. A new and distinct variety of *Chrysanthemum* plant named 'CIDZ0035' substantially as illustrated and described herein.

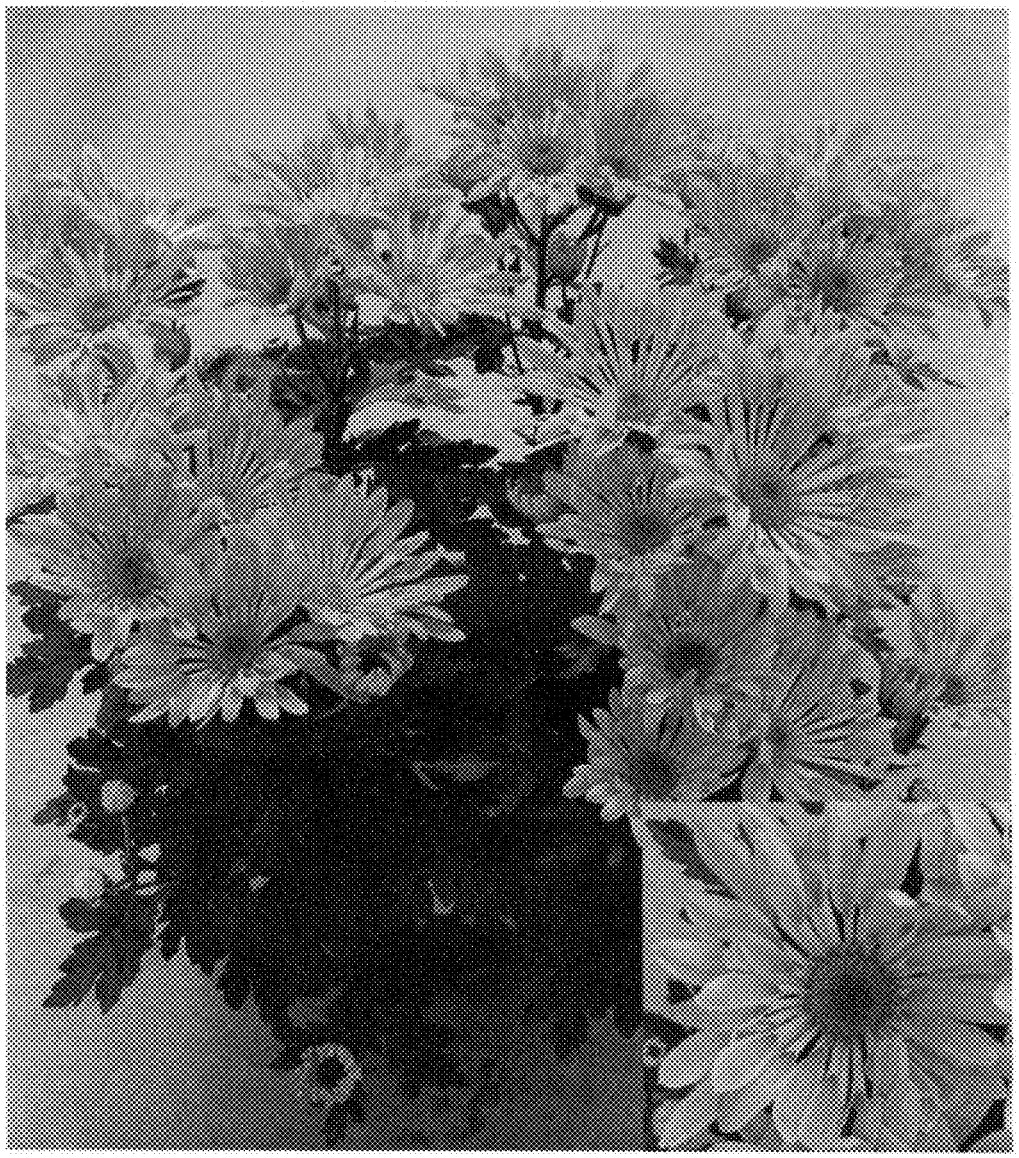

* * * * *